US00PP31873P2

(12) United States Plant Patent
Whitcomb

(10) Patent No.: US PP31,873 P2
(45) Date of Patent: Jun. 16, 2020

(54) ***LAGERSTROEMIA INDICA* PLANT NAMED 'WHIT XI'**

(50) Latin Name: *Lagerstroemia indica*
Varietal Denomination: Whit XI

(71) Applicant: Lacebark, Inc., Stillwater, OK (US)

(72) Inventor: Carl E. Whitcomb, Stillwater, OK (US)

(73) Assignee: Lacebark, Inc., Stillwater, OK (US)

( * ) Notice: Subject to any disclaimer, the term of this patent is extended or adjusted under 35 U.S.C. 154(b) by 0 days.

(21) Appl. No.: 16/350,910

(22) Filed: Feb. 1, 2019

(51) Int. Cl.
*A01H 5/02* (2018.01)
*A01H 6/00* (2018.01)

(52) U.S. Cl.
USPC ..... Plt./252
CPC ..... *A01H 6/00* (2018.05)

(58) Field of Classification Search
USPC ..... Plt./252
CPC ..... A01H 5/02
See application file for complete search history.

*Primary Examiner* — Kent L Bell
(74) *Attorney, Agent, or Firm* — Jeffrey Streets

(57) ABSTRACT

A new and distinct variety of *Lagerstroemia indica*, commonly known as crapemyrtle, named 'Whit XI', particularly distinguished by having a unique complex of highly modified sepals on a network of large, loose panicle-like structures. The plant does not produce flowers. The leaves are simple, alternate with a smooth margin, typical of the species. Young leaves emerge slightly crimson-green, maturing to dark green. Inflorescences are comprised of a network of irregular stem structures terminating in highly modified panicles with highly modified sepals, at first light purple in color, darkening with age to a darker purple and finally to brown. The inflorescences grow in a network over the surface of the plant and appear and function somewhat like normal flowers. As the modified sepals age they turn brown, but at the same time the panicle continues to grow slowly, producing new sepals light purple in color, which continues the appearance of flowering.

4 Drawing Sheets

Genus, species: *Lagerstroemia indica.*
Varietal denomination: 'WHIT XI'.

BACKGROUND OF THE INVENTION

Field of the Invention

The present invention relates to a new and distinct variety or cultivar of the ornamental shrub, *Lagerstroemia indica*, commonly known as crapemyrtle.

Description of the Related Art

*Lagerstroemia indica* is native to the eastern foothills of the Himalayan mountains in China and has been in cultivation in North America since about 1786. Initially only seedlings were grown, then it was discovered that asexual propagation was possible, giving rise to an assortment of cultivars.

Crapemyrtle flower on new growth with the onset of summer's heat and full sunshine. Typical flowering begins in late June or early July under Oklahoma conditions, followed by production of seed capsules, with no further flowering until seeds are mature.

In the USA, an assortment of seedlings have been selected, given varietal names and introduced into the nursery trade. Criteria for selection have been flower color, size of panicles, and other growth features, and resistance to powdery mildew and in recent years, *Cercospora* leaf spot disease.

SUMMARY OF THE INVENTION

The plant of the present invention is a new and distinct variety of crapemyrtle, *Lagerstroemia indica*, which has been given the cultivar name 'Whit XI' and is characterized by a unique complex of highly modified sepals on a network of large, loose panicle-like structures. The plant does not produce flowers.

The new sterile crapemyrtle variety claimed herein, which has been given the cultivar name 'Whit XI' is a never seen before unique seedling, most likely a naturally occurring variant or mutant seedling from a block of about 14,000 seedlings planted in 2016, which were 21 generational descendents from the original parent used to begin this research in 1986.

This new and distinct crapemyrtle was asexually propagated by softwood cuttings taken from the original 'Whit XI' plant near Stillwater, Okla. The asexually reproduced plants show all of the unique features that characterize this crapemyrtle. As a further test, cuttings were taken from the asexually propagated plants. These secondary cuttings rooted and grew the same as the parent, indicating that the unique features of this plant are stable through successive generations of asexual reproduction.

Leaves are simple, alternate with a smooth margin, typical of the species. Young leaves emerge slightly crimson-green, maturing to dark green and have remained free of both powdery mildew and *Cercospora* leaf spot.

Inflorescences are comprised of a network of irregular stem structures terminating in highly modified panicles with highly modified sepals, at first light purple in color, darkening with age to a darker purple and finally to brown. The inflorescences grow in a network over the surface of the plant and appear and function somewhat like normal flowers. As the modified sepals age they turn brown, but at the same time the panicle continues to grow slowly, producing new sepals light purple in color, which continues the appearance of flowering. Late in the growing season, new sepals cease to form, then the overall appearance shifts to a dark purple, then finally brown.

There are no flowers on the plant.

Emergence of the complex panicle network occurs in mid-summer, similar to typical crapemyrtle cultivars and remain attractive in Oklahoma for 40 to 60 days or longer depending on growing conditions and moisture.

BRIEF DESCRIPTIONS OF THE DRAWINGS

DETAILED BOTANICAL DESCRIPTION

Figure 1:
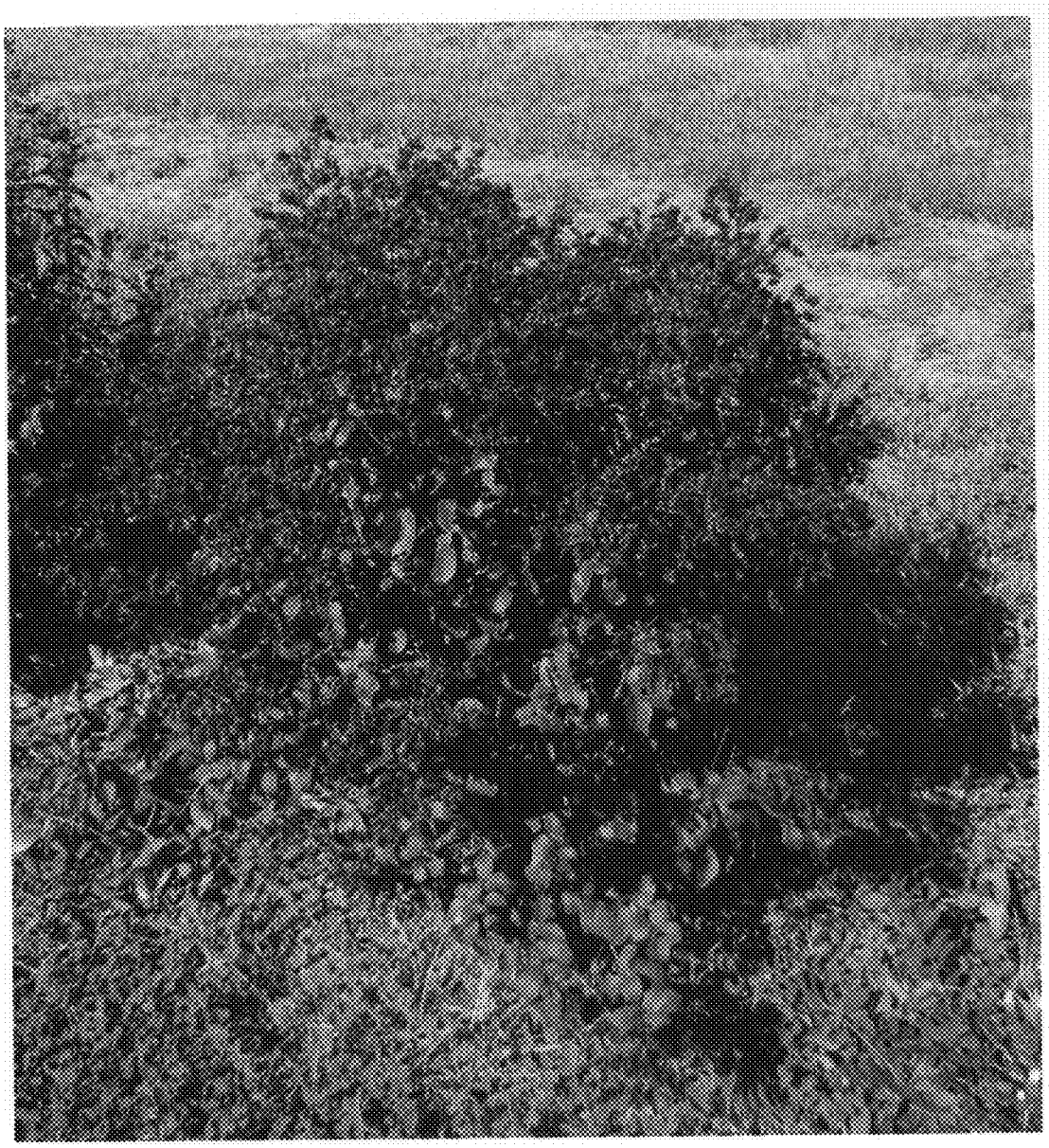
FIG. 1 is a full color photographic view of our new and highly unusual crapemyrtle plant 'Whit XI' at an age of three years from seed germination showing dense growth habit with flower-like panicles at the terminals of most branches and disease free dark green foliage.
Figure 2:
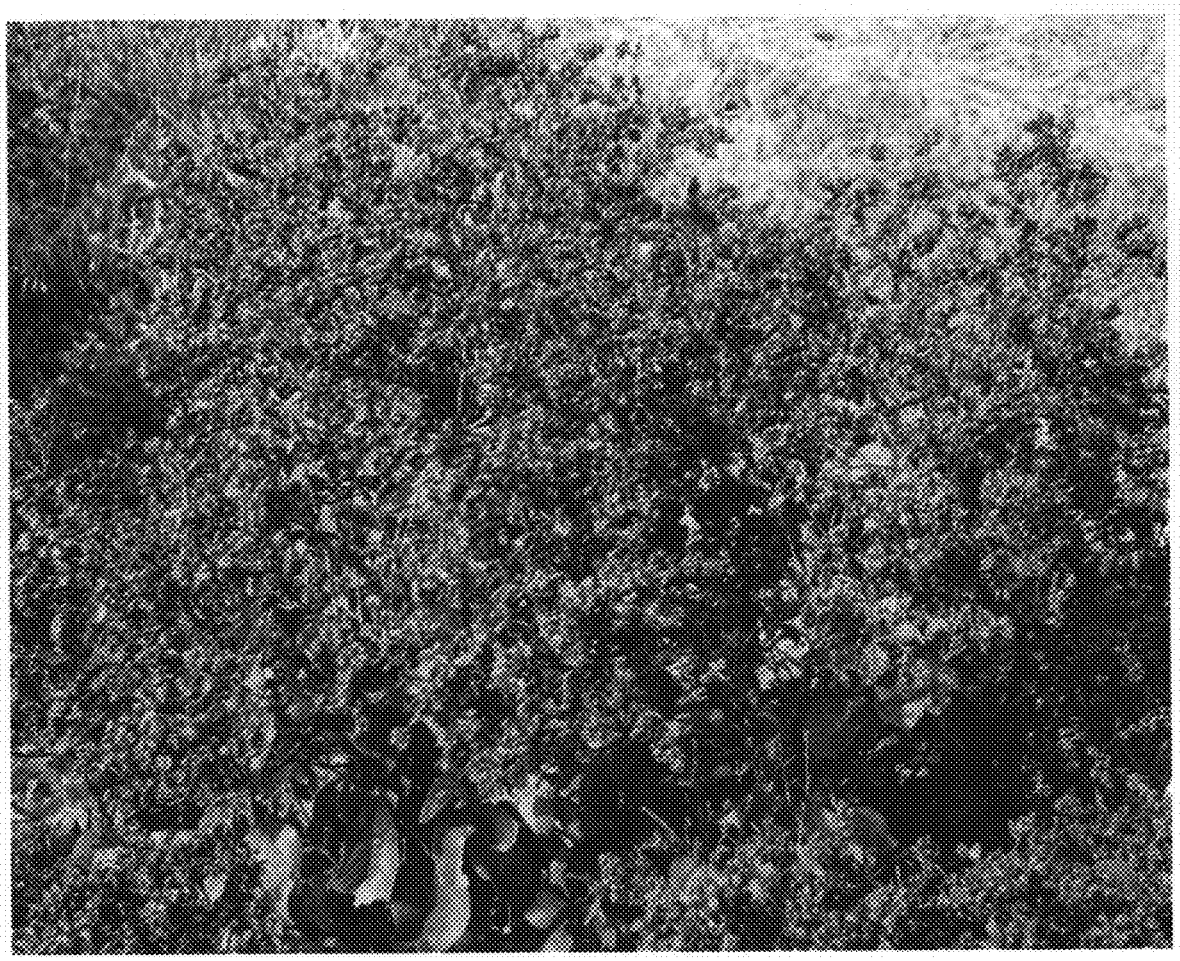
FIG. 2 is a full color photographic view of our new crapemyrtle plant 'Whit XI' at an age of three years from seed germination showing a complex network of panicle-like structures at the ends of most branches creating a flower-like appearance.

The following botanical description is of the new and distinct cultivar of crapemyrtle, *Lagerstroemia indica*, which has been given the cultivar name, 'WHIT XI'. Specific color designations set forth by number designations are in accordance with The Royal Horticultural Society Colour Chart (1966). General color recitations are consistent with ordinary American color terminology.

The plant:

*Type*.—Deciduous woody shrub with multiple stems and dense branching.

*Classification*.—Crapemyrtle, *Lagerstroemia indica*.

*Growth habit*.—The plant produces multiple stems creating a dense, upright shrub.

*Origin*.—In 1986, seed from one crapemyrtle plant was collected and planted. The resulting seedlings that showed signs of powdery mildew were culled, and seeds from the remaining few plants were planted to obtain another generation of seedlings. Following about eight generations, the number of seedlings culled due to powdery mildew was very small and in more recent seedling generations none have shown susceptibility to powdery mildew. This procedure continued until a population of about 14,000 seedlings planted in 2016 were 21 generations from the original crapemyrtle. This procedure is estimated to have involved approximately 700,000 seedlings. The plant named 'WHIT XI' is unlike any crapemyrtle among the large numbers of seedlings grown, unlike the original crapemyrtle, and unlike other known crapemyrtle plants. More specifically, 'Whit XI' cultivar is unlike any of its parents, grandparents, great-grandparents, etc. back 21 generations. 'Whit XI' grows and looks like other crapemyrtle seedlings early in the growing season, however, when other plants begin to form panicles of flowers, 'Whit XI' produces a totally novel network of highly modified panicles and what appear to be sepals.

*Propagation*.—The plant is easy to propagate from softwood cuttings under intermittent mist with the distinguishing characteristics of the asexually propagated offspring remaining identical to the parent.

*Size and shape*.—Growth of crapemyrtle, 'Whit XI' cultivar in an open field near Stillwater, Okla. is a multiple stemmed, upright shrub with a growth rate of 12 to 18 inches in height per year and 12 to 18 inches or more in spread per year. At 3 years of age, the plant had a height of approx. 28 inches and a spread of approx. 24 to 28 inches. It is estimated that crapemyrtle 'Whit XI' cultivar may reach a height of 6 to 8 feet with a spread of 4.5 to 6.0 feet. The estimated size of the plant is based on the observed three years of growth of 'Whit XI'.

*Hardiness*.—The new variety of crapemyrtle has withstood temperatures in the field near Stillwater, Okla. of about 0 F. with no injury.

*Pests and disease*.—Highly resistant to powdery mildew and *Cercospora* leaf spot which in recent decades has become a major problem on crapemyrtle. Crapemyrtle cultivar 'Whit XI' has retained a full complement of leaves to the end of the growing season while adjacent seedlings in the same row have been severely damaged by *Cercospora* disease.

The flowers:

*Blooming period*.—The plant produces no flowers. However, emergence of the unique complex of highly modified sepals on a network of large loose panicle-like structures begins in mid July in North Central Oklahoma and remain attractive for 40 to 60 days, depending on weather conditions and moisture.

*Petals*.—None, as there are no flowers.

*Inflorescences*.—A network of large, loose, panicle-like structures supporting a network of highly modified sepals that create the appearance that the plant is covered with small flowers.

*Stamens*.—None.

Figure 3:
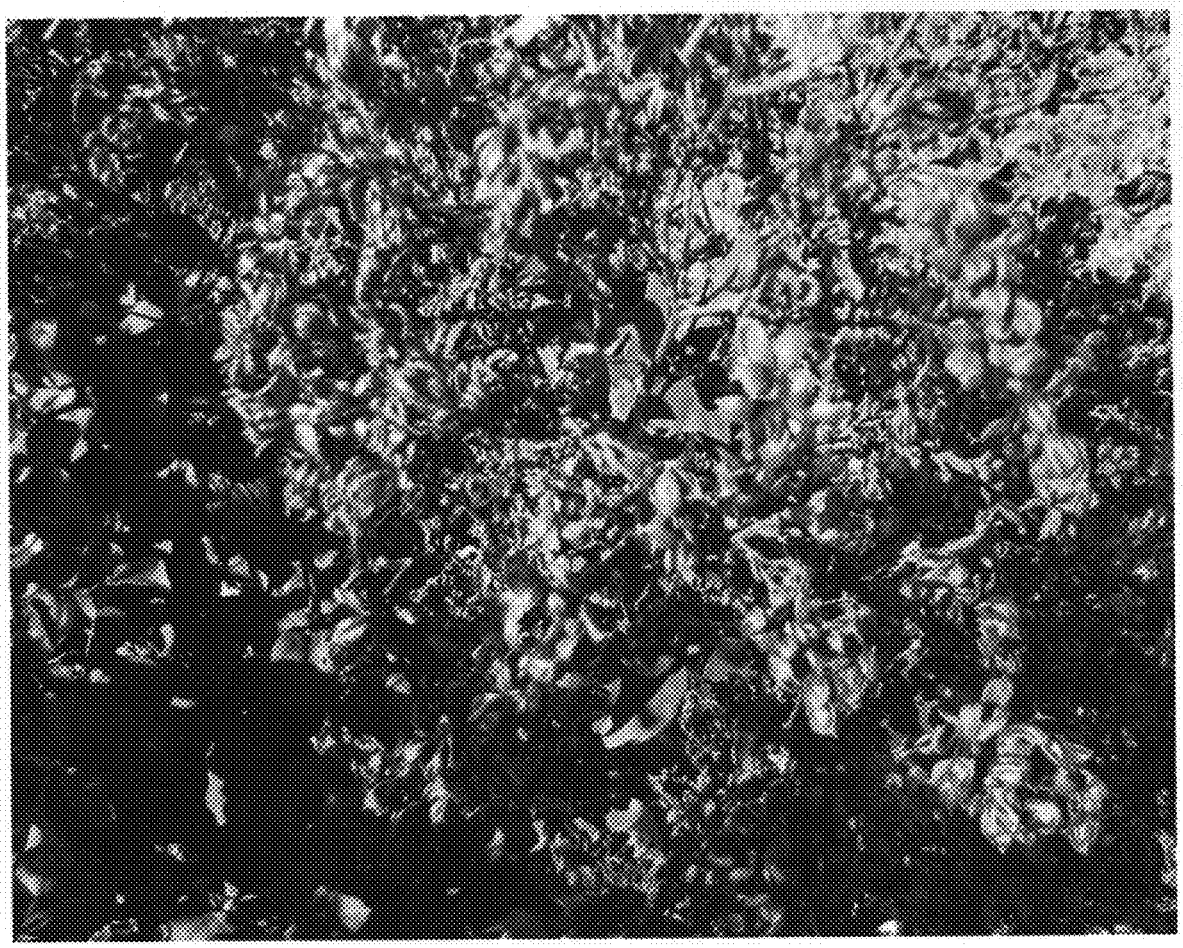
FIG. 3 is a full color photographic view of our new crapemyrtle plant 'Whit XI' at an age of three years from seed germination showing the complex of younger purple modified sepals having been produced at the ends of panicle like structures and older brown and shriveled sepals below.
Figure 4:
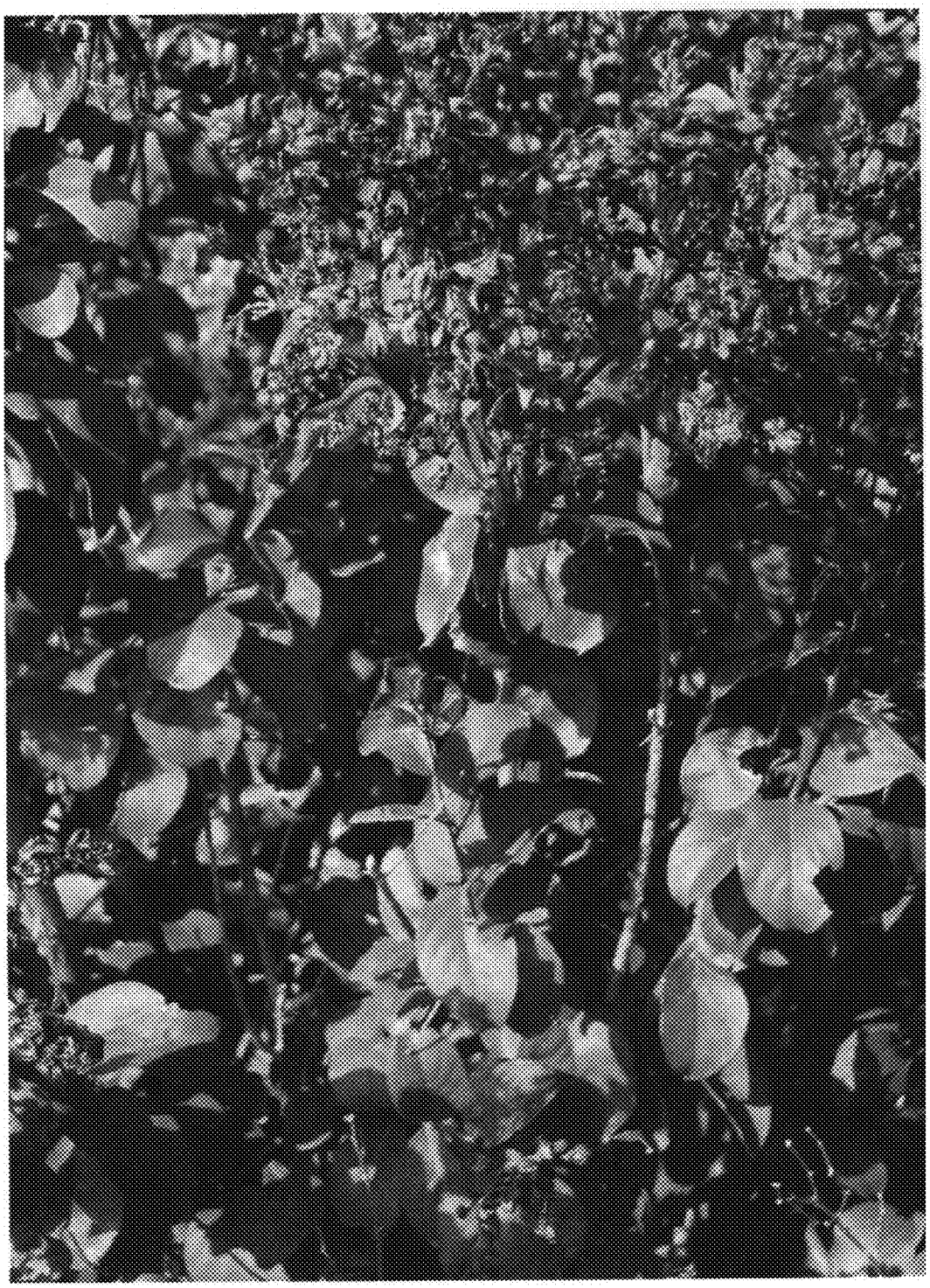
FIG. 4 is a full color photographic view of our new crapemyrtle plant 'Whit XI' at an age of three years from seed germination showing several of the highly modified panicle-structures supporting highly modified sepals with dense dark green disease free leaves below.

*Sepals*.—Sepals are irregularly dispersed across the outer portions of the network of large, loose, panicle-like structures. Emergence of sepals are approximately greyed-purple group 187-D or C, then during the growing season, sepals shrivel and turn brown, approximately 177-B or C, but with a progressing development of new sepals that are 187-D or C, (see FIG. 3 for visual details). As the season progresses, and with no new sepal production, the network of highly modified large, loose, panicle-like structures darken to approximately 187-A or B (see FIG. 1 for visual details).

*Buds*.—This plant, 'Whit XI', does not produce flower buds, but transitions from vegetative growth to this most peculiar network of large, loose, panicle-like structures. As such, there is no notable and observable bud to describe.

*Seeds*.—No flowers or seed capsule-like structures are produced.

The foliage:

*Leaf shape*.—Leaves are simple, sessile, alternately arranged on the stems and ovate to obovate in overall form and either obtuse or mucronate at the apex with a herring-bone venation pattern, glabrous and with a smooth margin.

*Leaf color*.—Leaves emerge slightly crimson-green approximately 197-C or D, maturing to approximately 139-A or B on both upper and lower leaf surfaces including vein color on upper and lower surfaces of the leaf blade.

*Leaf texture*.—Leaves are glabrous on both upper and lower surfaces.

*Leaf size*.—Leaf size ranges from about 1.25 to 2.25 inches long by 1.0 to 1.5 inches wide.

The branches and bark:

*Branch color*.—Branches are about 177-C or D when young, transitioning to about 177-A or B at maturity.

*Branch length*.—Early season branches are typically about 6 to 12 inches long, while mid-summer branches are about 4 to 8 inches depending on season and growing conditions.

*Branch diameter*.—Branch diameter ranges from about ⅛ to ¼ inch diameter.

*Bark*.—Smooth when young, soon developing shallow ribs or lines parallel with the stem with age and about 177-A, B or C.

I claim:

1. A new and distinct variety of crapemyrtle plant, *Lagerstroemia indica*, substantially as illustrated and described.

* * * * *